United States Patent
Fickel et al.

(10) Patent No.: US 11,203,558 B2
(45) Date of Patent: Dec. 21, 2021

(54) SELECTIVE HYDROGENOLYSIS INTEGRATED WITH CRACKING

(71) Applicants: Sabic Global Technologies, B.V., Bergen Op Zoom (NL); Dustin Fickel, Sugar Land, TX (US); Heng Shou, Sugar Land, TX (US)

(72) Inventors: Dustin Fickel, Sugar Land, TX (US); Heng Shou, Sugar Land, TX (US)

(73) Assignee: Sabic Global Technologies, B.V., Bergen Op Zoom (NL)

(*) Notice: Subject to any disclaimer, the term of this patent is extended or adjusted under 35 U.S.C. 154(b) by 0 days.

(21) Appl. No.: 17/262,286

(22) PCT Filed: Sep. 17, 2019

(86) PCT No.: PCT/US2019/051463
§ 371 (c)(1),
(2) Date: Jan. 22, 2021

(87) PCT Pub. No.: WO2020/061010
PCT Pub. Date: Mar. 26, 2020

(65) Prior Publication Data
US 2021/0331988 A1    Oct. 28, 2021

Related U.S. Application Data (60) Provisional application No. 62/733,284, filed on Sep. 19, 2018.

(51) Int. Cl.
*C07C 4/06* (2006.01)
*B01J 29/44* (2006.01)
(Continued)

(52) U.S. Cl.
CPC ............... *C07C 4/06* (2013.01); *B01J 29/44* (2013.01); *C07C 5/52* (2013.01); *C07C 7/005* (2013.01); *C07C 2529/44* (2013.01)

(58) Field of Classification Search
CPC .. C07C 4/06; C07C 5/52; C07C 7/005; C07C 2529/44; B01J 29/44; C10G 47/16
See application file for complete search history.

(56) References Cited

U.S. PATENT DOCUMENTS

| 4,137,147 A | 1/1979 | Franck et al. |
| 4,140,621 A | 2/1979 | Franck et al. |

(Continued)

FOREIGN PATENT DOCUMENTS

| CN | 107223119 A | 9/2017 |
| WO | 2012071137 A1 | 5/2012 |

(Continued)

OTHER PUBLICATIONS

Filing Receipt, Specification and Drawings for U.S. Appl. No. 62/733,284, entitled "Selective Hydrogenolysis Integrated with Cracking," filed Sep. 19, 2018, 41 pages.

(Continued)

*Primary Examiner* — Thuan D Dang
(74) *Attorney, Agent, or Firm* — Rodney B. Carroll; Conley Rose, P.C.

(57) ABSTRACT

A process for producing olefins comprising introducing butane feed (n-butane, i-butane) and hydrogen to hydrogenolysis reactor comprising hydrogenolysis catalyst to produce a hydrogenolysis product stream (hydrogen, methane, ethane, propane, i-butane, optionally n-butane, optionally $C_{5+}$ hydrocarbons); and feeding the hydrogenolysis product stream and hydrogen to hydrocracking reactor comprising a hydrocracking catalyst to produce hydrocracking product stream (hydrogen, methane, ethane, propane, i-butane, (Continued)

optionally n-butane), wherein the amount of i-butane in the hydrocracking product stream is less than in the hydrogenolysis product stream, and wherein the amount of ethane in the hydrocracking product stream is greater than in the hydrogenolysis product stream. The hydrocracking product stream is separated into first hydrogen stream, first methane stream, first $C_{2+}$ gas stream (ethane, propane), first $C_4$s stream (i-butane, optionally n-butane), optionally $C_{5+}$ stream; and the first $C_{2+}$ gas stream is fed to gas steam cracker to produce a steam cracker product stream comprising olefins (ethylene, propylene).

20 Claims, 3 Drawing Sheets

(51) Int. Cl.
*C07C 5/52* (2006.01)
*C07C 7/00* (2006.01)

(56) References Cited

U.S. PATENT DOCUMENTS

| | | |
|---|---|---|
| 4,166,077 A | 8/1979 | Bernard et al. |
| 4,680,355 A | 7/1987 | Nakahara et al. |
| 9,011,672 B2 | 4/2015 | Etter et al. |
| 9,850,438 B2 | 12/2017 | Oprins |
| 2008/0029434 A1 | 2/2008 | Brewer et al. |
| 2008/0128324 A1 | 6/2008 | Hansen et al. |
| 2016/0362617 A1 | 12/2016 | Oprins et al. |
| 2017/0369795 A1 | 12/2017 | Oprins et al. |
| 2018/0117566 A1 | 5/2018 | Witte et al. |

FOREIGN PATENT DOCUMENTS

| | | |
|---|---|---|
| WO | 2017072698 A1 | 5/2017 |
| WO | 2017089938 A1 | 6/2017 |
| WO | 2020061010 A1 | 3/2020 |
| WO | 2020061012 A1 | 3/2020 |

OTHER PUBLICATIONS

Filing Receipt, Specification and Drawings for U.S. Appl. No. 62/733,309, entitled "Bimetallic Catalysts Supported on Zeolites for Selective Conversion of N-Butane to Ethane," filed Sep. 19, 2018, 44 pages.
Foreign Communication from Related Application—International Search Report and Written Opinion of the International Searching Authority, International Application No. PCT/US2019/051463, dated Jan. 3, 2020, 11 pages.
Foreign Communication from Related Application—International Search Report and Written Opinion of the International Searching Authority, International Application No. PCT/US2019/051470, dated Jan. 3, 2020, 10 pages.
Bernard, J.R., et al., "A Selective Route for the Hydrogenolysis of Alkanes into Ethane," Studies in Surface Science and Catalysis, 1981, pp. 149-159, vol. 7.
Bond, Geoffrey C., et al., "Hydrogenolysis of Propane, n-Butane, and Isobutane over Variously Pretreated Ru/TiO2 Catalysts," Journal of Physical Chemistry, 1986, pp. 4877-4881, vol. 90, No. 20, American Chemical Society.
Jackson, S.D. et al., "Supported Metal Catalysts; Preparation, Characterisation, and Function; Part IV. Hydrogenolysis of Ethane, Propane, n-Butance and iso-Butane over Supported Platinum Catalysts" Journal of Catalysis, 1998, pp. 225-234, vol. 176, Academic Press.
Kozlov, I.T. et al., "Selective Hydrocracking of Light Naphtha Cuts," Chemistry and Technology of Fuels and Oils, Jul. 1985, pp. 346-349, vol. 21, No. 7, Plenum Publishing Corporation.
Sinfelt, J.H., "Catalytic Hydrogenolysis on Metals," Catalysis Letters, 1991, pp. 159-172, vol. 9, J.C. Baltzer A.G. Scientific Publishing Company.

SELECTIVE HYDROGENOLYSIS INTEGRATED WITH CRACKING

CROSS REFERENCE TO RELATED APPLICATION

This application is a filing under 35 U.S.C. 371 of International Application No. PCT/US2019/051463, filed Sep. 17, 2019, entitled "Selective Hydrogenolysis Integrated with Cracking," which claims priority to U.S. Provisional Application No. 62/733,284, filed Sep. 19, 2018, which applications are incorporated by reference herein in their entirety.

TECHNICAL FIELD

The present disclosure relates to methods of producing olefins, more specifically methods of producing light olefins, such as ethylene and propylene.

BACKGROUND

Hydrocarbons, and specifically olefins such as ethylene and propylene, are typically building blocks used to produce a wide range of products, for example, break-resistant containers and packaging materials. Currently, for industrial scale applications, ethylene is produced by cracking natural gas condensates and petroleum distillates, which include ethane and higher hydrocarbons (e.g., butanes), and the produced ethylene is separated from a product mixture by using gas separation processes. When higher hydrocarbons (e.g., butanes) are cracked, such cracking can generate a significant amount of undesired methane, $C_{3+}$ compounds, and heavies, thereby demanding an intensive separation process and lowering the overall efficiency of the process, especially towards desired light olefins such as ethylene. Thus, there is an ongoing need for the development of processes for the production of light olefins, such as ethylene and propylene.

BRIEF DESCRIPTION OF THE DRAWINGS

For a detailed description of the preferred aspects of the disclosed methods, reference will now be made to the accompanying drawing in which.

DETAILED DESCRIPTION

Disclosed herein are processes integrating a butane hydrogenolysis reactor with a hydrocracking reactor, wherein a feed stream to the process comprises a mixed butane stream (e.g., field-grade butane). Generally, field-grade butane streams comprise a mixture of n-butane and i-butane; for example from about 60 mol % to about 75 mol % n-butane, and from about 25 mol % to about 40 mol % i-butane (e.g., a mole ratio of n-butane to i-butane of from about 1:1 to about 4:1). By using a hydrogenolysis catalyst in a hydrogenolysis reactor, field-grade butane streams can be reactively separated via selectively reacting the n-butane from the field-grade butane streams. A hydrogenolysis reactor can convert the n-butane to a gaseous stream of methane, ethane, and propane (predominately ethane; and specifically more ethane than a comparative hydrocracking reactor cracking the same amount of n-butane). Hydrogen can be co-fed with the field-grade butane stream to the hydrogenolysis reactor. The hydrogenolysis catalyst can comprise a variety of monometallic catalysts (e.g., Pt or Ir supported on alumina, and/or Pt or Ir supported on ZSM-5) and/or bimetallic catalysts (e.g., Pt and Ir supported on alumina, and/or Pt and Ir supported on ZSM-5).

Generally, i-butane is minimally converted in the hydrogenolysis reactor (e.g., the hydrogenolysis reactor can be characterized by an i-butane conversion of less than about 25%). The hydrogenolysis reaction can be run with operational parameters (e.g., catalyst, pressure, temperature, flow rate, etc.) effective for limiting (e.g., minimizing, reducing, etc.) i-butane conversion, thus resulting in high ethane selectivity. Without wishing to be limited by theory, when i-butane is converted, 1 mole of i-butane generally converts to 1 mole of methane and 1 mole of propane (i.e., no ethane); and by avoiding or minimizing i-butane conversion, the overall ethane selectivity can be increased. Further, n-butane is generally converted almost entirely in the hydrogenolysis reactor (i.e., n-butane conversion is maximized in the hydrogenolysis reactor); for example the hydrogenolysis reactor can be characterized by an n-butane conversion of greater than about 90%. The hydrogenolysis reaction can be run with operational parameters effective for maximizing (e.g., enhancing, increasing, etc.) n-butane conversion, thus resulting in high ethane selectivity. Without wishing to be limited by theory, when n-butane is converted, 1 mole of n-butane generally converts to 2 moles of ethane; and by maximizing n-butane conversion, the overall ethane selectivity can be increased. The process for producing olefins as disclosed herein can maximize the production of ethane in the hydrogenolysis reaction. As will be appreciated by one of skill in the art, and with the help of this disclosure, as the conversion of n-butane undesirably lessens in the hydrogenolysis reactor and/or as more i-butane is undesirably converted in the hydrogenolysis reactor, the amount of ethane produced and/or the ethane selectivity, respectively, decrease in the hydrogenolysis reactor.

The i-butane recovered from the hydrogenolysis reactor can be fed to a hydrocracking reactor, wherein i-butane can be converted to a mixture of methane, ethane, and propane; although the amount of ethane produced in the hydrocracking reactor is less than the amount of ethane produced in the hydrogenolysis reactor, according to a process for producing olefins from a field-grade butane stream as disclosed herein. By integrating the hydrogenolysis with the hydrocracking in series, an overall higher amount of ethane can be produced from a field-grade butane stream, than if only hydrocracking were to be employed. The ethane can be further sent to a steam cracking furnace for ethylene production.

While the current disclosure will be discussed in detail in the context of a butane feed stream being introduced to a hydrogenolysis reactor for the reactive separation of i-butane from n-butane, it should be understood that any suitable type of hydrocarbon feed stream can be introduced to a hydrogenolysis reactor as disclosed herein for the reactive separation of its components; for example a naphtha feed stream.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having equal to or greater than x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

Figure 1:
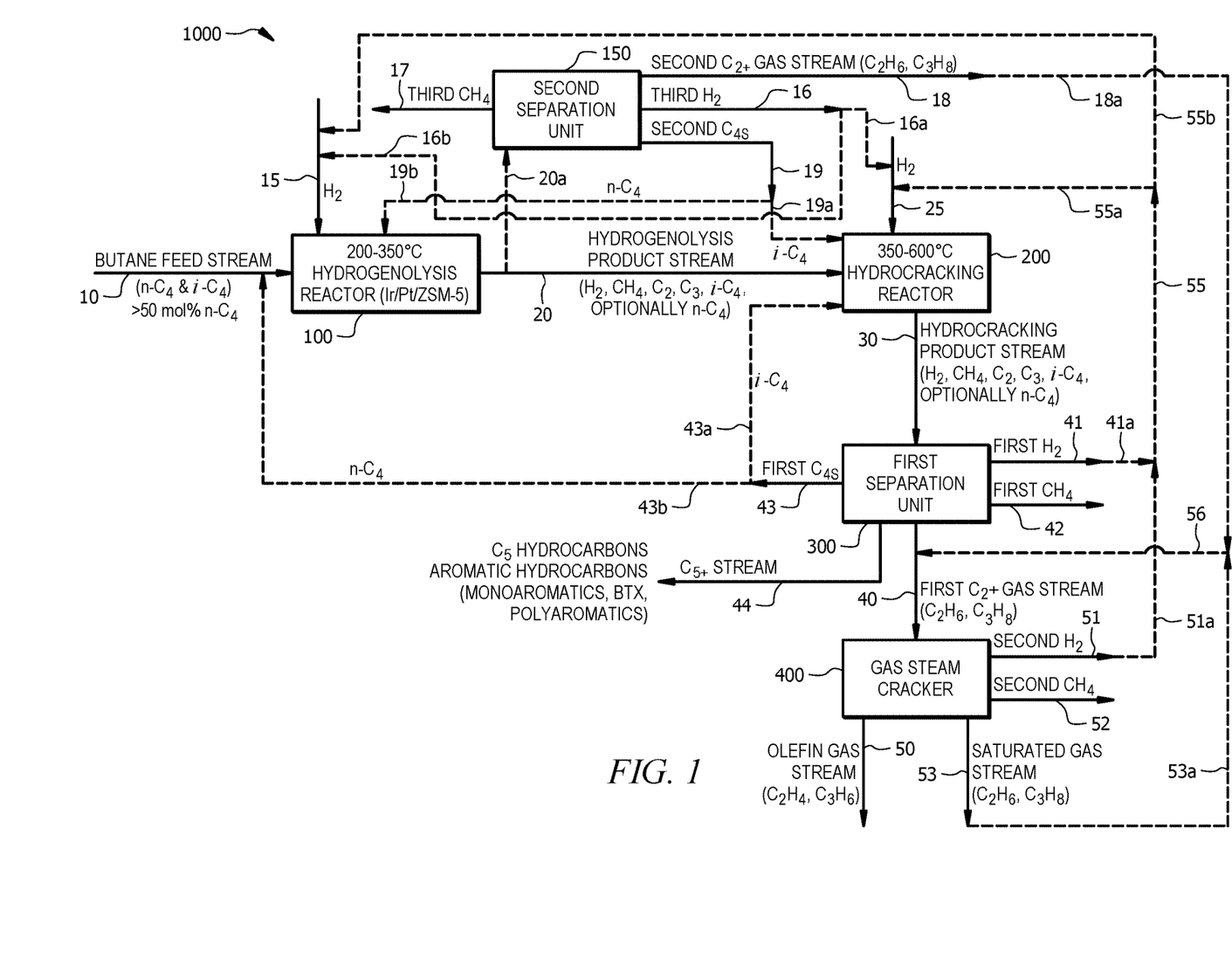
FIG. 1 displays a configuration of an olefins production system.

Referring to FIG. 1, an olefins production system 1000 is disclosed. The olefins production system 1000 generally comprises a hydrogenolysis reactor 100; a hydrocracking reactor 200; a first separation unit 300; a gas steam cracker 400; and optionally a second separation unit 150. As will be appreciated by one of skill in the art, and with the help of this disclosure, olefins production system components shown in FIG. 1 can be in fluid communication with each other (as represented by the connecting lines indicating a direction of fluid flow) through any suitable conduits (e.g., pipes, streams, etc.).

In an aspect, the process for producing olefins as disclosed herein can comprise introducing a butane feed stream 10 and hydrogen 15 to the hydrogenolysis reactor 100 to produce a hydrogenolysis product stream 20, wherein the hydrogenolysis reactor 100 comprises a hydrogenolysis catalyst, wherein the butane feed stream 10 comprises n-butane and i-butane, and wherein the hydrogenolysis product stream 20 comprises hydrogen, methane, ethane, propane, i-butane, and optionally n-butane. In some aspects, the hydrogenolysis product stream 20 can further comprise some impurities, such as $C_{5+}$ hydrocarbons. In some aspects, the hydrogenolysis product stream 20 is substantially free of n-butane.

Generally, hydrogenolysis refers to a chemical reaction whereby a carbon-carbon or carbon-heteroatom single bond is cleaved or undergoes "lysis" by hydrogen, usually at relatively low temperatures (e.g., less than about 330° C.). For purposes of the disclosure herein, the term "selective hydrogenolysis" refers to a hydrogenolysis process wherein two or more different hydrocarbons (e.g., first hydrocarbon, second hydrocarbon; n-butane, i-butane) are subjected to a hydrogenolysis reaction, and wherein at least one hydrocarbon (e.g., first hydrocarbon; n-butane) undergoes hydrogenolysis, and wherein at least one hydrocarbon (e.g., second hydrocarbon; i-butane) is resistant to hydrogenolysis (e.g., has a low conversion in a hydrogenolysis reaction, such as less than about 25% conversion), under the same given set of reaction conditions (e.g., catalyst, pressure, temperature, flow rate, etc.). Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. Without wishing to be limited by theory, the hydrogenolysis reaction rate of the first hydrocarbon (e.g., n-butane) is greater than the hydrogenolysis reaction rate of the second hydrocarbon (e.g., i-butane), thereby allowing the separation (e.g., reactive separation) of n-butane and i-butane by consuming the n-butane in the hydrogenolysis reaction and recovering the unreacted i-butane. As will be appreciated by one of skill in the art, and with the help of this disclosure, the selective hydrogenolysis of n-butane from a butane feed stream (e.g., butane feed stream 10) comprising n-butane and i-butane provides for the reactive separation of n-butane from i-butane.

In an aspect, the butane feed stream 10 can comprise n-butane and i-butane. In some aspects, the butane feed stream 10 can comprise n-butane in an amount of equal to or greater than about 5 mol %, alternatively equal to or greater than about 10 mol %, alternatively equal to or greater than about 20 mol %, alternatively equal to or greater than about 30 mol %, alternatively equal to or greater than about 40 mol %, alternatively equal to or greater than about 50 mol %, alternatively equal to or greater than about 60 mol %, alternatively equal to or greater than about 70 mol %, alternatively equal to or greater than about 80 mol %, or alternatively equal to or greater than about 90 mol %.

The butane feed stream 10 can comprise i-butane in an amount of equal to or greater than about 5 mol %, alternatively equal to or greater than about 10 mol %, alternatively equal to or greater than about 20 mol %, alternatively equal to or greater than about 30 mol %, alternatively equal to or greater than about 40 mol %, alternatively equal to or greater than about 50 mol %, alternatively equal to or greater than about 60 mol %, alternatively equal to or greater than about 70 mol %, alternatively equal to or greater than about 80 mol %, or alternatively equal to or greater than about 90 mol %.

In an aspect, the butane feed stream 10 can be characterized by a mole ratio of n-butane to i-butane of equal to or greater than about 0.05:1, alternatively equal to or greater than about 0.1:1, alternatively equal to or greater than about 0.25:1, alternatively equal to or greater than about 0.5:1, alternatively equal to or greater than about 1:1, alternatively equal to or greater than about 2:1, alternatively equal to or greater than about 2.5:1, alternatively equal to or greater than about 5:1, alternatively equal to or greater than about 7.5:1, alternatively equal to or greater than about 10:1, alternatively from about 0.05:1 to about 10:1, alternatively from about 0.1:1 to about 7.5:1, alternatively from about 0.25:1 to about 5:1, or alternatively from about 0.5:1 to about 2.5:1.

In an aspect, the butane feed stream 10 can comprise n-butane in an amount of equal to or greater than about 50 mol %. In such aspect, the butane feed stream 10 can comprise i-butane in an amount of less than about 50 mol %.

In an aspect, the butane feed stream 10 can comprise field grade-butane (e.g., mixed butane). Field-grade butane is generally produced by natural gas processing and/or oil refining. Field-grade butane can comprise from about 50 mol % to about 80 mol %, alternatively from about 55 mol % to about 80 mol %, or alternatively from about 60 mol % to about 75 mol % n-butane; and from about 20 mol % to about 50 mol %, alternatively from about 20 mol % to about 45 mol %, or alternatively from about 25 mol % to about 40 mol % i-butane. Field-grade butane can further comprise from about 0 mol % to about 5 mol % propane and/or pentanes. In some aspects, the field-grade butane can be characterized by a mole ratio of n-butane to i-butane of from about 1:1 to about 4:1, alternatively from about 1.2:1 to about 4:1, or alternatively from about 1.5:1 to about 3:1.

In an aspect, the hydrogenolysis reactor 100 can comprise a fixed bed reactor, a radial flow reactor, a multi-layered bed reactor, a continuous flow reactor, an adiabatic reactor, an isothermal reactor, and the like, or combinations thereof.

In an aspect, the hydrogenolysis reactor 100 can be characterized by a temperature (e.g., hydrogenolysis temperature) of from about 200° C. to about 330° C., alternatively from about 250° C. to about 325° C., or alternatively from about 280° C. to about 310° C. As will be appreciated by one of skill in the art, and with the help of this disclosure, temperatures below 330° C. are conducive to selective hydrogenolysis. By contrast to hydrogenolysis, hydrocracking refers to a process that rearranges and breaks hydrocarbon chains, as well as adds hydrogen to unsaturated hydrocarbons to produce saturated hydrocarbons, at relatively high temperatures (e.g., greater than about 330° C.).

As will be appreciated by one of skill in the art, and with the help of this disclosure, and without wishing to be limited by theory, given the same feed stream, hydrogenolysis and hydrocracking will produce a different product distribution, owing to different reaction mechanisms, which can activate or inhibit different components of a given catalyst. For example, relatively high temperatures (e.g., hydrocracking temperatures, such as greater than about 400° C.) can inactivate one of the metals of a hydrogenolysis catalyst (e.g., a metal of a hydrogenolysis bimetallic supported catalyst, such as Ir), thereby promoting cracking and hydrogenation of all components of the feed stream (e.g., n-butane and i-butane) in the presence of the partially inactivated hydrogenolysis catalyst. Further, as will be appreciated by one of skill in the art, and with the help of this disclosure, and without wishing to be limited by theory, relatively high temperatures (e.g., hydrocracking temperatures, such as greater than about 400° C.) are generally needed to get over the activation energy to begin cracking. Furthermore, as will be appreciated by one of skill in the art, and with the help of this disclosure, and without wishing to be limited by theory, the branched i-butane is a more stable molecule than the linear n-butane, and as such higher temperatures (e.g., greater than about 400° C.) are generally necessary to activate i-butane in a cracking process.

In an aspect, hydrogenolysis of the butane feed stream 10 at relatively low temperatures (e.g., less than about 330° C.) can increase the amount of ethane in the hydrogenolysis product stream 20, as compared to the amount of ethane in a product stream obtained from an otherwise similar process that would be run at relatively high temperatures (e.g., greater than about 330° C.).

As will be appreciated by one of skill in the art, and with the help of this disclosure, hydrocracking of a butane feed stream at relatively high temperatures (e.g., greater than about 330° C.) can increase the amount of propane and/or methane in the product stream, as compared to the amount of propane and/or methane, respectively in a product stream obtained from an otherwise similar process (e.g., hydrogenolysis process) that is run at relatively low temperatures (e.g., less than about 330° C.). Further, as will be appreciated by one of skill in the art, and with the help of this disclosure, and without wishing to be limited by theory, hydrocracking follows a different reaction mechanism or pathway as compared to hydrogenolysis, which leads to an increased amount of propane in hydrocracking as compared to hydrogenolysis.

The hydrogenolysis reactor 100 can be characterized by a pressure (e.g., hydrogenolysis pressure) of from about 0 psig to about 300 psig, alternatively from about 10 psig to about 300 psig, alternatively from about 20 psig to about 200 psig, alternatively from about 50 psig to about 150 psig, alternatively from about 75 psig to about 125 psig, or alternatively from about 90 psig to about 110 psig.

The hydrogenolysis reactor 100 can be characterized by a hydrocarbon-based weight hourly space velocity (WHSV) of from about 0.1 $h^{-1}$ to about 15 $h^{-1}$, alternatively from about 0.5 $h^{-1}$ to about 10 $h^{-1}$, or alternatively from about 1 $h^{-1}$ to about 5 $h^{-1}$. Generally, the WHSV refers to a mass of reagents (e.g., hydrocarbons) fed per hour divided by a mass of catalyst used in a particular reactor.

The hydrogenolysis reactor 100 can be characterized by a hydrogen to $C_4$ hydrocarbons molar ratio of from about 1:1 to about 10:1, alternatively from about 1.5:1 to about 7.5:1, or alternatively from about 2:1 to about 5:1.

In some aspects, the hydrogenolysis reactor 100 can be operated under an optimal set of operational parameters that result in substantially consuming all of the n-butane in the hydrogenolysis reactor 100, wherein the hydrogenolysis product stream 20 is substantially free of n-butane. For example, in order to substantially consume all of the n-butane in the hydrogenolysis reactor 100, the hydrogenolysis reactor 100 can be operated at a WHSV of from about 3 $h^{-1}$ to about 5 h$^{-1}$, a pressure of from about 50 psig to about 100 psig, a hydrogen to C$_4$ hydrocarbons molar ratio of from about 2:1 to about 2.5:1, at a temperature of from about 280° C. to about 300° C.; and in the presence of a hydrogenolysis bimetallic supported catalyst comprising Pt and Ir supported on ZSM-5, wherein Pt is present in a total amount of from about 0.2 wt. % to about 0.4 wt. %, or alternatively about 0.3 wt. %, based on the total weight of the hydrogenolysis bimetallic supported catalyst; wherein Ir is present in a total amount of from about 0.2 wt. % to about 0.4 wt. %, or alternatively about 0.3 wt. %, based on the total weight of the hydrogenolysis bimetallic supported catalyst; wherein Pt and Ir are present in a weight ratio of Pt to Ir of from about 0.8:1 to about 1.2:1, or alternatively about 1:1; and wherein the ZSM-5 is characterized by a weight ratio of silica to alumina (SiO$_2$/Al$_2$O$_3$) of from about 250 to about 300, or alternatively about 280.

In an aspect, the hydrogenolysis reactor 100 can comprise a hydrogenolysis catalyst. In some aspects, the hydrogenolysis catalyst can comprise a hydrogenolysis monometallic supported catalyst, such as a zeolite-supported monometallic catalyst and/or an alumina-supported monometallic catalyst. In other aspects, the hydrogenolysis catalyst can comprise a hydrogenolysis bimetallic supported catalyst, such as a zeolite-supported bimetallic catalyst and/or an alumina-supported bimetallic catalyst. In yet other aspects, the hydrogenolysis catalyst can comprise a hydrogenolysis monometallic supported catalyst and a hydrogenolysis bimetallic supported catalyst.

In some aspects, a hydrogenolysis bimetallic supported catalyst as disclosed herein can comprise a first metal, a second metal, and a support; wherein the first metal and the second metal are different. In other aspects, a hydrogenolysis monometallic supported catalyst as disclosed herein can comprise a third metal and a support. In some aspects, the third metal can be the same as the first metal or the second metal. In other aspects, the third metal can be the different from the first metal and/or the second metal.

In an aspect, the first metal, the second metal, and the third metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co).

In an aspect, the first metal, the second metal, and the third metal can each independently be one or more metals from Group 6 of the Periodic Table; one or more metals from Group 8 of the Periodic Table; one or more metals from Group 9 of the Periodic Table; one or more metals from Group 10 of the Periodic Table; or combinations thereof; wherein the first metal and the second metal are different; and wherein the third metal is the same as or different from the first metal and/or the second metal.

In some aspects, the first metal comprises Pt, and the second metal comprises Ir. In other aspects, the first metal comprises Pt, and the second metal comprises Rh. In yet other aspects, the first metal comprises Pt, and the second metal comprises Ir and Rh.

In some aspects, the third metal can comprise, Pt, Ir, or Rh.

In an aspect, the first metal and the second metal can be present in the hydrogenolysis bimetallic supported catalyst in a weight ratio of first metal to second metal of from about 0.1:1 to about 10:1, alternatively from about 0.5:1 to about 7:1, alternatively from about 1:1 to about 4:1, alternatively from about 0.3:1 to about 3:1, alternatively from about 0.5:1 to about 2:1, alternatively from about 0.7:1 to about 1.5:1, or alternatively from about 0.8:1 to about 1.2:1.

In an aspect, the first metal and the second metal can be present in the hydrogenolysis bimetallic supported catalyst in a total amount (i.e., first metal amount+second metal amount) of from about 0.1 wt. % to about 10 wt. %, alternatively from about 0.15 wt. % to about 5 wt. %, alternatively from about 0.2 wt. % to about 1 wt. %, alternatively from about 0.4 wt. % to about 0.8 wt. %, or alternatively from about 0.5 wt. % to about 0.7 wt. %, based on the total weight of the hydrogenolysis bimetallic supported catalyst.

In an aspect, the third metal can be present in the hydrogenolysis monometallic supported catalyst in a total amount of from about 0.1 wt. % to about 10 wt. %, alternatively from about 0.15 wt. % to about 5 wt. %, alternatively from about 0.2 wt. % to about 1 wt. %, alternatively from about 0.4 wt. % to about 0.8 wt. %, or alternatively from about 0.5 wt. % to about 0.7 wt. %, based on the total weight of the hydrogenolysis monometallic supported catalyst.

In an aspect, the support suitable for use in the hydrogenolysis catalyst of the current disclosure can comprise alumina and/or a zeolite.

In some aspects, the support suitable for use in the hydrogenolysis catalyst of the current disclosure can consist of or consist essentially of alumina and/or a zeolite. In other aspects, the support suitable for use in the hydrogenolysis catalyst of the current disclosure can comprise alumina and/or a zeolite; and a binder. Generally a binder can be used to improve mechanical properties of a support (e.g., improve resistance to attrition). Nonlimiting examples of binders suitable for use in the hydrogenolysis catalyst as disclosed herein include alumina, titania, silica, and the like, or combinations thereof.

In an aspect, a hydrogenolysis catalyst as disclosed herein can comprise an alumina support. For purposes of the disclosure herein the term "alumina support(s)" includes any suitable type of alumina (Al$_2$O$_3$), such as alpha alumina, beta alumina, gamma alumina, eta alumina, theta alumina, amorphous alumina, and the like, or combinations thereof.

In an aspect, a hydrogenolysis catalyst as disclosed herein can comprise a zeolitic support. For purposes of the disclosure herein the term "zeolitic support(s)" includes zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof. Further, for purposes of the disclosure herein, zeolitic structures, zeolitic frameworks, aluminosilicates, aluminosilicates structures, aluminosilicates frameworks, zeolite-type materials, zeolite-type structures, zeolite-type frameworks, molecular sieves, silicoaluminophosphates, silicoaluminophosphates structures, silicoaluminophosphates frameworks, aluminophosphates, aluminophosphates structures, aluminophosphates frameworks, and the like, or combinations thereof are referred to herein collectively as "zeolites."

The zeolitic support can comprise zeolites such as small pore zeolites, medium pore zeolites, large pore zeolites, or combinations thereof. Zeolites are inorganic crystalline solids having a framework structure with channels and cavities with characteristic pore geometry. Zeolites can be classified according to their pore openings. For example, small pore zeolites have 8 membered ring pore openings, which can be characterized by a pore size (e.g., diameter of the pore opening) of from 3 Å to 4.5 Å; medium pore zeolites have 10 membered ring pore openings, which can be characterized by a pore size (e.g., diameter of the pore opening) of from 4.5 Å to 6.0 Å; and large pore zeolites have 12 membered ring pore openings, which can be characterized by a pore size (e.g., diameter of the pore opening) of from 6.0 Å to 8.0 Å.

In some aspects, the zeolitic support can comprise one or more aluminosilicate zeolites containing $SiO_4$ and $AlO_4$ tetrahedra in their structure (e.g., framework structure). In other aspects, the zeolitic catalyst can comprise a zeolite-type material, such as silicoaluminophosphates (SAPOs) containing $PO_4$, $AlO_4$ and $SiO_4$ tetrahedra in the structure (e.g., framework structure); and/or aluminophosphates (AlPOs) containing $PO_4$, and $AlO_4$ tetrahedra in the structure (e.g., framework structure). The $SiO_4$, $AlO_4$ and/or $PO_4$ tetrahedra share oxygen atoms, wherein the framework structures have well defined channels and cavities (e.g., pores). These cavities may generally contain exchangeable cations, such as $H^+$, $Na^+$ and $K^+$. Without wishing to be limited by theory, in the zeolite framework structure or zeolite-type framework structure, Si or Al or P can be partially substituted by other tri-valent or tetra-valent elements, such as Ge, Ga, B, etc. Further, and without wishing to be limited by theory, in zeolites, Si or Al or P can also be partially substituted by one or more elements selected from the group consisting of titanium, nickel, copper, magnesium, tin, cobalt, iron, zinc, tungsten, vanadium, gallium, calcium, manganese, ruthenium and rhenium.

Without wishing to be limited by theory, zeolites are generally characterized by a certain acidity, owing to the presence of Brønsted acid sites and/or Lewis acid sites. In zeolites, a Brønsted acidic proton can be a hydrogen atom bonded to the oxygen atom that connects the tetrahedrally coordinated aluminum which forms the zeolite structural framework. The Lewis acid centers in zeolites can contain tri-coordinated aluminum sites, which are electron deficient sites exhibiting the ability to accept electrons during interactions with molecules. In some aspects, the zeolite suitable for use in the zeolitic support as disclosed herein can be treated to reduce its acidity, for example by titration with a basic salt containing $Na^+$ and/or $K^+$ cations (e.g., by impregnation, ion-exchange, etc.). As will be appreciated by one of skill in the art, and with the help of this disclosure, and without wishing to be limited by theory, acidic sites in a zeolite can promote isomerization of n-butane to i-butane. In some aspects, the zeolitic support can be characterized by low acidity and/or low aluminum content; e.g., the zeolitic support can be characterized by low Brønsted acidity. In some aspects, the zeolitic support can be characterized by substantially no acidity (i.e., zero acidity).

In some aspects, the zeolitic support can be characterized by a weight ratio of silica to alumina ($SiO_2/Al_2O_3$) of equal to or greater than about 100, alternatively equal to or greater than about 150, alternatively equal to or greater than about 200, alternatively equal to or greater than about 250, alternatively equal to or greater than about 275, alternatively equal to or greater than about 300, alternatively from about 100 to about 400, alternatively from about 200 to about 350, alternatively from about 250 to about 300, alternatively from about 275 to about 290, or alternatively about 280. In an aspect, the zeolitic support (e.g., ZSM-5) can be characterized by a weight ratio of silica to alumina ($SiO_2/Al_2O_3$) of 280. As will be appreciated by one of skill in the art, and with the help of this disclosure, and without wishing to be limited by theory, the acidity of a support decreases with increasing its weight ratio of silica to alumina ($SiO_2/Al_2O_3$).

In an aspect, the zeolitic support can comprise a zeolite, wherein the zeolite can be selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof.

In some aspects, a zeolitic support can comprise from about 70 wt. % to about 90 wt. %, alternatively from about 75 wt. % to about 85 wt. %, or alternatively about 80 wt. % zeolite; and from about 10 wt. % to about 30 wt. %, alternatively from about 15 wt. % to about 25 wt. %, or alternatively about 20 wt. % binder (e.g., alumina binder); based on the total weight of the zeolitic support.

In an aspect, the zeolitic support can be present in the hydrogenolysis bimetallic supported catalyst in an amount of from about 90 wt. % to about 99.9 wt. %, alternatively from about 95 wt. % to about 99.85 wt. %, or alternatively from about 99 wt. % to about 99.8 wt. %, based on the total weight of the hydrogenolysis bimetallic supported catalyst.

In an aspect, a hydrogenolysis bimetallic supported catalyst as disclosed herein can comprise a first metal, a second metal, and a zeolitic support; wherein the first metal comprises Pt, wherein the second metal comprises Ir, and wherein the zeolitic support comprises ZSM-5.

The hydrogenolysis bimetallic supported catalyst as disclosed herein can be prepared by any suitable methodology, for example as described in more detail in U.S. Provisional Patent Application No. 62/733,309, filed Sep. 19, 2018, which is incorporated by reference herein in its entirety.

In an aspect, the hydrogenolysis bimetallic supported catalyst as disclosed herein can be characterized by a selectivity to ethane of from about 60 mol % to about 90 mol %, alternatively from about 65 mol % to about 85 mol %, or alternatively from about 70 mol % to about 80 mol %. Generally, a selectivity to a desired product or products refers to how much desired carbon product was formed divided by the total carbon products formed, both desired and undesired. For purposes of the disclosure herein, the selectivity to a desired product is a % selectivity based on moles converted into the desired product.

In an aspect, the hydrogenolysis bimetallic supported catalyst as disclosed herein can be characterized by a selectivity to methane of less than about 20 mol %, alternatively less than about 15 mol %, or alternatively less than about 12.5 mol %.

In an aspect, the hydrogenolysis bimetallic supported catalyst as disclosed herein can be characterized by a selectivity to propane of less than about 15 mol %, alternatively less than about 12.5 mol %, or alternatively less than about 10 mol %.

In an aspect, the hydrogenolysis reactor 100 can be characterized by an i-butane conversion that is less than an n-butane conversion. As will be appreciated by one of skill in the art, and with the help of this disclosure, the conversion of reagents in hydrogenolysis is dependent on a variety of reactor conditions, such as flow rate, temperature, etc.

In an aspect, the hydrogenolysis reactor 100 can be characterized by an i-butane conversion of less than about 25%, alternatively less than about 20%, alternatively less than about 15%, alternatively less than about 10%, alternatively less than about 5%, alternatively less than about 1%, alternatively less than about 0.5%, alternatively less than about 0.1%, alternatively less than about 0.01%, or alternatively less than about 0.001%.

In an aspect, the hydrogenolysis reactor 100 can be characterized by a n-butane conversion of equal to or greater than about 75%, alternatively equal to or greater than about 80%, alternatively equal to or greater than about 85%, alternatively equal to or greater than about 90%, alternatively equal to or greater than about 95%, or alternatively equal to or greater than about 99%. In some aspects, the hydrogenolysis reactor 100 can be characterized by an n-butane conversion of 100%. In some aspects, substantially all of the n-butane introduced to the hydrogenolysis reactor 100 is converted; e.g., the hydrogenolysis product stream 20 is substantially free of n-butane.

In some aspects, the hydrogenolysis reactor 100 can be characterized by an i-butane conversion of less than about 25%, and by a n-butane conversion of equal to or greater than about 90%.

In an aspect, the process for producing olefins as disclosed herein can comprise feeding at least a portion of the hydrogenolysis product stream 20 and hydrogen 25 to the hydrocracking reactor 200 to produce a hydrocracking product stream 30, wherein the hydrocracking product stream 30 comprises hydrogen, methane, ethane, propane, i-butane, optionally n-butane, optionally $C_5$ hydrocarbons, and optionally $C_{6+}$ aromatic hydrocarbons, and wherein the amount of i-butane in the hydrocracking product stream 30 is less than the amount of i-butane in the hydrogenolysis product stream 20. $C_{5+}$ hydrocarbons (e.g., $C_5$ hydrocarbons; $C_{6+}$ aromatic hydrocarbons, monoaromatics, such as benzene, toluene, xylene (BTX), polyaromatics, etc.) can be produced in the hydrocracker as heavier liquid by-products. For example, the hydrocracking product stream 30 can comprise less than about 10 wt. %, alternatively less than about 5 wt. %, or alternatively less than about 3 wt. % $C_{5+}$ hydrocarbons, based on the total weight of the hydrocracking product stream 30.

In an aspect, the hydrocracking reactor 200 can comprise a fixed bed reactor, a radial flow reactor, an adiabatic reactor, a single bed reactor, a multiple bed reactor, and the like, or combinations thereof. In some aspects, the hydrocracking reactor 200 can comprise single bed reactors connected in series. In other aspects, the hydrocracking reactor 200 can comprise a single reactor with multiple beds. In yet other aspects, the hydrocracking reactor 200 can comprise at least a single bed reactor and at least a single reactor with multiple beds, wherein the reactors and/or the beds can be arranged in any suitable configuration (e.g., in series and/or in parallel). The hydrocracking reactor 200 can comprise any suitable reactor configuration.

The hydrocracking reactor 200 can be characterized by a temperature (e.g., hydrocracking temperature) of from about 350° C. to about 600° C., alternatively from about 375° C. to about 550° C., or alternatively from about 400° C. to about 525° C.

The hydrocracking reactor 200 can be characterized by a pressure (e.g., hydrocracking pressure) of from about 10 psig to about 300 psig, alternatively from about 50 psig to about 275 psig, alternatively from about 100 psig to about 250 psig, alternatively from about 125 psig to about 225 psig, or alternatively from about 150 psig to about 200 psig.

The hydrocracking reactor 200 can be characterized by a hydrocarbon-based weight hourly space velocity (WHSV) of from about 0.1 $h^{-1}$ to about 10 $h^{-1}$, alternatively from about 0.5 $h^{-1}$ to about 7.5 $h^{-1}$, or alternatively from about 1 $h^{-1}$ to about 5 $h^{-1}$.

The hydrocracking reactor 200 can be characterized by a hydrogen to $C_4$ hydrocarbons molar ratio of from about 0.75:1 to about 10:1, alternatively from about 1:1 to about 9:1, alternatively from about 1.5:1 to about 7.5:1, or alternatively from about 2:1 to about 5:1.

The hydrocracking reactor 200 can comprise a hydrocracking catalyst. The hydrocracking catalyst can comprise one or more metals on a support. The combination of the one or more metals and support is catalytically active in a hydrocracking reaction. As would be appreciated by one of skill in the art, and with the help of this disclosure, the one or more metals can be catalytically active for hydrogenation reactions, and the support can be catalytically active for cracking reactions. Generally, hydrocracking reactions can crack (break down) larger hydrocarbons (e.g., the hydrocarbons of the hydrogenolysis product stream 20) into smaller hydrocarbons, as well as saturate unsaturated hydrocarbons (e.g., olefins) that could be produced during cracking, such that the hydrocracking product stream 30 comprises saturated small chain hydrocarbons (e.g., ethane, propane).

Nonlimiting examples of the one or more metals suitable for use in the hydrocracking catalyst of the current disclosure can comprise Pd, Pt, Ni, Co, Mn, Fe, Rh, Ir, Ru, W, Zr, and the like, or combinations thereof.

In an aspect, the one or more metals can be present in the hydrocracking catalyst in an amount of from about 0.01 wt. % to about 2.5 wt. %, alternatively from about 0.02 wt. % to about 1 wt. %, or alternatively from about 0.05 wt. % to about 0.5 wt. %, based on a total weight of the hydrocracking catalyst.

Nonlimiting examples of the support suitable for use in the hydrocracking catalyst of the current disclosure can comprise a zeolite, ZSM-5, zeolite Y, mordenite, zeolite L, ZSM-22, ZSM-11, chabazite, ferrierite, zeolite beta, silated ZSM-5, zirconia, sulfated zirconia, alumina, and the like, or combinations thereof. In an aspect, the hydrocracking catalyst can comprise Pt on ZSM-5. In some aspects, the support suitable for use in the hydrocracking catalyst of the current disclosure can comprise a zeolite characterized by a Si:Al ratio of from about 50 to about 200, or alternatively from about 100 to about 200.

In an aspect, the support suitable for use in the hydrocracking catalyst of the current disclosure can comprise an alumina support and/or a zeolitic support of the type disclosed herein for the hydrogenolysis catalyst.

In some aspects, the hydrocracking catalyst can comprise a hydrogenolysis catalyst as disclosed herein, for example a hydrogenolysis bimetallic supported catalyst as disclosed herein. The hydrocracking catalyst and the hydrogenolysis catalyst can be the same or different.

In an aspect, the amount of ethane in the hydrocracking product stream 30 is greater than the amount of ethane in the hydrogenolysis product stream 20. In an aspect, the hydrogenolysis catalyst can be characterized by a selectivity to ethane that is greater than a selectivity to ethane of the hydrocracking catalyst. However, and as will be appreciated by one of skill in the art, and with the help of this disclosure, while the hydrogenolysis catalyst can be more selective towards ethane as compared to the hydrocracking catalyst, the hydrocracking product stream 30 will contain more ethane than the hydrogenolysis product stream 20, because the hydrogenolysis product stream 20 is introduced to the hydrocracking reactor 200, and as such the ethane present in the hydrogenolysis product stream 20 is substantially recovered in the hydrocracking product stream 30, in addition to the ethane that is produced in the hydrocracking reactor 200. Further, and as will be appreciated by one of skill in the art, and with the help of this disclosure, although a small portion (e.g., less than about 10%) of the ethane introduced to the hydrocracking reactor 200 could be cracked to methane and/or dehydrogenated to ethylene, most of the ethane introduced to the hydrocracking reactor 200 is recovered in the hydrocracking product stream 30.

In an aspect, an ethane to propane weight ratio in the hydrocracking product stream 30 is increased by equal to or greater than about 10%, alternatively by equal to or greater than about 15%, alternatively by equal to or greater than about 20%, or alternatively by equal to or greater than about 25%, when compared to an ethane to propane weight ratio in a hydrocracking product stream in an otherwise similar process that lacks a step of introducing a butane feed stream and hydrogen to a hydrogenolysis reactor (e.g., in an otherwise similar process that uses a hydrocracking reactor only, and no hydrogenolysis reactor).

In an aspect, the process for producing olefins as disclosed herein can comprise feeding at least a portion of the hydrocracking product stream 30 to the first separation unit 300 to yield a first $C_{2+}$ gas stream 40, a first hydrogen stream 41, a first methane stream 42, a first $C_4$s stream 43, and optionally a $C_{5+}$ stream 44, wherein the first $C_{2+}$ gas stream 40 comprises ethane and propane, wherein the first $C_4$s stream 43 comprises i-butane, and optionally n-butane; and wherein the $C_{5+}$ stream 44 comprises $C_5$ hydrocarbons, and optionally $C_{6+}$ aromatic hydrocarbons (e.g., monoaromatics, such as benzene, toluene, xylene (BTX), polyaromatics, etc.).

The first separation unit 300 can comprise any suitable separation unit that is configured to separate the hydrocracking product stream 30 into the first $C_{2+}$ gas stream 40, the first hydrogen stream 41, the first methane stream 42, the first $C_4$s stream 43, and optionally the $C_{5+}$ stream 44. For example, the first separation unit 300 can employ distillation, cryogenic distillation, extractive distillation, selective adsorption, selective absorption, and the like, or combinations thereof. The first separation unit 300 can comprise a distillation column, a cryogenic distillation column, a trayed and/or packed separation column, a compressor, a heat exchanger, a cooling tower, a pressure swing adsorption (PSA) unit, etc.

Generally, hydrogen can be recovered by using any suitable methodology, such as PSA, membrane separation, cryogenic separation, etc. In some aspects, hydrogen (e.g., high-purity hydrogen) can be recovered by using a PSA process which is based on a physical binding of gas molecules to adsorbent material, wherein forces acting between gas molecules and adsorbent material depend on the gas component, type of adsorbent material, partial pressure of the gas component and operating temperature. The separation effect is based on differences in binding forces to the adsorbent material. Highly volatile components with low polarity, such as hydrogen, are practically non-adsorbable, as opposed to molecules such as hydrocarbons, nitrogen, carbon monoxide, carbon dioxide, water vapor, etc., and as such high purity hydrogen can be recovered.

Individual hydrocarbons or hydrocarbon fractions can be usually recovered by fractionation processes that can employ a variety of columns, such as a cryogenic distillation column configuration comprising a demethanizer, a deethanizer, a depropanizer, etc.

In an aspect, the process for producing olefins as disclosed herein can comprise optionally feeding at least a portion 20a of the hydrogenolysis product stream 20 to the second separation unit 150 to yield a third hydrogen-containing stream 16, optionally a third methane stream 17, a second $C_{2+}$ gas stream 18, and a second $C_4$s stream 19, wherein the second $C_{2+}$ gas stream 18 comprises ethane and propane, and wherein the second $C_4$s stream 19 comprises i-butane, and optionally n-butane. In aspects where only a fairly low amount of methane is produced during hydrogenolysis (e.g., methane make is relatively low), methane could be separated along with the hydrogen, wherein the third hydrogen-containing stream 16 can comprise hydrogen and methane, and wherein a separate methane steam is not recovered. In such aspects, a purge can be taken off the third hydrogen-containing stream 16 (e.g., prior to recycling stream 16 to reactor 100 and/or reactor 200), for example to avoid build-up of methane in the reactor 100 and/or reactor 200.

The second separation unit 150 can comprise any suitable separation unit that is configured to separate the hydrogenolysis product stream 20 into the third hydrogen-containing stream 16, optionally the third methane stream 17, the second $C_{2+}$ gas stream 18, and the second $C_4$s stream 19. For example, the second separation unit 150 can employ distillation, cryogenic distillation, extractive distillation, selective adsorption, selective absorption, and the like, or combinations thereof. The second separation unit 150 can comprise a distillation column, a cryogenic distillation column, a trayed and/or packed separation column, a compressor, a heat exchanger, a cooling tower, a pressure swing adsorption (PSA) unit, etc.

In an aspect, the process for producing olefins as disclosed herein can comprise optionally feeding at least a portion of the first $C_4$s stream 43 and/or at least a portion of the second $C_4$s stream 19 to the hydrocracking reactor 200.

In some aspects, the first $C_4$s stream 43 and/or the second $C_4$s stream 19 comprise n-butane. In such aspects, at least a portion of the first $C_4$s stream 43 and/or at least a portion of the second $C_4$s stream 19 can be separated into an i-butane stream and an n-butane stream.

In aspects where the first $C_4$s stream 43 and/or the second $C_4$s stream 19 comprise n-butane, at least a portion of the first $C_4$s stream 43 and/or at least a portion of the second $C_4$s stream 19 can be recycled to the hydrogenolysis reactor 100; for example to allow for the reactive separation of n-butane from i-butane.

In an aspect, at least a portion of the first $C_4$s stream 43 can be separated into a first i-butane stream 43a and a first n-butane stream 43b; for example via cryogenic distillation. In an aspect, at least a portion of the second $C_4$s stream 19 can be separated into a second i-butane stream 19a and a second n-butane stream 19b; for example via cryogenic distillation.

In some aspects, at least a portion of the first i-butane stream 43a and/or at least a portion of the second i-butane stream 19a can be fed to the hydrocracking reactor 200. In some aspects, at least a portion of the first n-butane stream 43b and/or at least a portion of the second n-butane stream 19b can be fed to the hydrogenolysis reactor 100.

In an aspect, the process for producing olefins as disclosed herein can comprise feeding at least a portion of the first $C_{2+}$ gas stream 40, and optionally at least a portion 18a of the second $C_{2+}$ gas stream 18 (e.g., via stream 56) to the gas steam cracker 400 (e.g., gas steam cracker furnace) to produce a steam cracker product stream, wherein the steam cracker product stream comprises olefins, wherein the amount of olefins in the steam cracker product stream is greater than the amount of olefins in the first $C_{2+}$ gas stream 40, and optionally the second $C_{2+}$ gas stream 18, and wherein the olefins comprise ethylene and propylene. As will be appreciated by one of skill in the art, and with the help of this disclosure, the term "steam cracker" (e.g., gas steam cracker) can refer to a furnace section or portion of a steam cracker unit; or it can refer to both the furnace section and separation section of the steam cracker unit. The steam cracker product stream can comprise olefins, such as ethylene, propylene; saturated hydrocarbons, such as methane, ethane, propane, etc.; and hydrogen.

In an aspect, an ethylene to propylene weight ratio in the steam cracker product stream is increased by equal to or greater than about 10%, alternatively by equal to or greater than about 25%, alternatively by equal to or greater than about 50%, or alternatively by equal to or greater than about 75%, when compared to an ethylene to propylene weight ratio in a steam cracker product stream in an otherwise similar process that lacks a step of introducing a butane feed stream and hydrogen to a hydrogenolysis reactor (e.g., in an otherwise similar process that uses a hydrocracking reactor only, and no hydrogenolysis reactor). The use of a hydrogenolysis reactor (e.g., hydrogenolysis reactor 100) upstream of a hydrocracking reactor (e.g., hydrocracking reactor 200) can provide for an enhanced amount of ethane in the hydrocracking product stream (e.g., hydrocracking product stream 30), which in turn can result in an increased amount of ethylene (and less propylene) in the steam cracker product stream.

In an aspect, an ethylene to propylene weight ratio in the steam cracker product stream is equal to or greater than about 4:1, alternatively equal to or greater than about 5:1, or alternatively equal to or greater than about 6:1.

Generally, steam cracking is a process in which saturated hydrocarbons (i.e., alkanes) are converted into unsaturated hydrocarbons (i.e., olefins), for example via cracking and/or dehydrogenation in the presence of steam. In steam cracking, a hydrocarbon feed stream, such as the first $C_{2+}$ gas stream 40, and optionally the second $C_{2+}$ gas stream 18, is diluted with steam and briefly heated in a furnace, in the absence of oxygen, to produce olefins. As will be appreciated by one of skill in the art, and with the help of this disclosure, some steam crackers have specific feed requirements (depending on operating constraints of individual steam crackers), such as less than about 1 wt. % olefins in the feed, based on the total weight of the feed.

Further, as will be appreciated by one of skill in the art, and with the help of this disclosure, the composition of the steam cracker product stream depends on steam cracker parameters (e.g., temperature, residence time, hydrocarbon to steam ratio, etc.), as well as on the composition of the feed to the steam cracker. Heavier hydrocarbons feed streams can undesirably produce a substantial amount of heavier hydrocarbons (e.g., $C_{4+}$ hydrocarbons), in addition to light gas olefins (e.g., ethylene, propylene). Lighter feed streams, such as the first $C_{2+}$ gas stream 40, and optionally the second $C_{2+}$ gas stream 18, can generally produce a substantially higher amount of light gas olefins when compared to the amount of light gas olefins produced from heavier hydrocarbons feed streams.

As will be appreciated by one of skill in the art, and with the help of this disclosure, the composition of the feed to the steam cracker can vary, and optimal steam cracking of different feed components may occur at different temperatures. For example, ethane can be steam cracked to ethylene at a temperature that is higher than the optimal temperature for steam cracking propane to ethylene. As such, various components of the feed to the steam cracker can be introduced at different points within a steam cracker furnace, to provide for an optimum temperature for steam cracking individual components of the feed to the steam cracker (e.g., the first $C_{2+}$ gas stream 40, and optionally the second $C_{2+}$ gas stream 18). Further, and as will be appreciated by one of skill in the art, and with the help of this disclosure, while propylene is always produced in some amount during steam cracking, propylene will be produced in smaller amounts at higher cracking temperatures.

Furthermore, as will be appreciated by one of skill in the art, and with the help of this disclosure, the heavier the feed component, the lower the temperature required for cracking the component. For example, propane requires a cracking temperature that is lower than a cracking temperature of ethane. In aspects where components of the feed to the gas steam cracker 400 are not or cannot be separated into individual components and where ethylene is the main target product, the first $C_{2+}$ gas stream 40, and optionally the second $C_{2+}$ gas stream 18 can be introduced to the gas steam cracker furnace at a point where the component requiring the highest temperature can be steam cracked. For example, if the feed to the gas steam cracker 400 comprises both ethane and propane, the feed can be introduced to the to the gas steam cracker furnace at the point where the temperature is high enough to crack ethane, as propane would also be cracked at that temperature. As will be appreciated by one of skill in the art, and with the help of this disclosure, the decision of where to introduce the feed into the furnace or furnace section can be made based on the desired product(s). For example, if ethylene is the desired product, a higher temperature can be employed than when propylene is the desired product.

In some aspects, the gas steam cracker 400 can comprise a plurality of steam cracking furnaces (e.g., cracking zones), wherein at least some of the steam cracking furnaces can operate at temperatures different from each other, to provide for efficiently cracking individual components of the first $C_{2+}$ gas stream 40, and optionally the second $C_{2+}$ gas stream 18. In other aspects, a gas steam cracking furnace can comprise a plurality of cracking zones within the same gas steam cracking furnace, wherein at least some of the cracking zones can operate at temperatures different from each other, to provide for efficiently cracking individual components of the first $C_{2+}$ gas stream 40, and optionally the second $C_{2+}$ gas stream 18.

In some aspects, at least a portion of the first $C_{2+}$ gas stream 40, and optionally at least a portion of the second $C_{2+}$ gas stream 18 can be separated into an ethane stream and a propane stream, for example by cryogenic distillation.

In an aspect, the gas steam cracker furnace can comprise a first cracking zone and a second cracking zone, wherein the first cracking zone is characterized by a first cracking temperature (e.g., an ethane cracking temperature; a temperature effective for steam cracking ethane), wherein the second cracking zone is characterized by a second cracking temperature (e.g., a propane cracking temperature; a temperature effective for steam cracking propane), and wherein the first cracking temperature is greater than the second cracking temperature. Ethane (e.g., ethane stream) can be fed to the first cracking zone. Propane (e.g., propane stream) can be fed to the second cracking zone. In aspects where ethane and propane are not or cannot be separated into individual components, both ethane and propane can be fed to the first cracking zone and/or to the second cracking zone. As will be appreciated by one of skill in the art, and with the help of this disclosure, if more ethylene is desired as a product, then both ethane and propane can be fed to the cracking zone with the higher temperature (e.g., first cracking zone); and if more propylene is desired as a product, then both ethane and propane can be fed to the cracking zone with the lower temperature (e.g., second cracking zone). Multi-zone cracking furnaces are described in more detail in U.S. Publication No. 20080029434 A1, which is incorporated by reference herein in its entirety.

In some aspects, at least a portion of the propane stream can be fed to a propane dehydrogenation unit to produce propylene.

In some aspects, the same gas steam cracking furnace can comprise the first cracking zone and the second cracking zone. In other aspects, a first cracking furnace can comprise the first cracking zone and a second cracking furnace can comprise the second cracking zone.

In an aspect, the process for producing olefins as disclosed herein can comprise separating at least a portion of the steam cracker product stream in a steam cracker separation unit into an olefin gas stream 50, a second hydrogen stream 51, a second methane stream 52, and a saturated gas stream 53; wherein the olefin gas stream 50 comprises ethylene and propylene; and wherein the saturated gas stream 53 comprises ethane and propane. The steam cracker product stream can further comprise pygas and/or pyoil which are formed as byproducts from the steam cracker, and as such the pygas and/or pyoil can be separated in the steam cracker separation unit as well.

The steam cracker separation unit can comprise any suitable separation unit that is configured to separate the steam cracker product stream into the olefin gas stream 50, the second hydrogen stream 51, the second methane stream 52, the saturated gas stream 53, and optionally pygas and/or pyoil. For example, the steam cracker separation unit can employ distillation, cryogenic distillation, extractive distillation, selective adsorption, selective absorption, and the like, or combinations thereof. The steam cracker separation unit can comprise a distillation column, a cryogenic distillation column, a trayed and/or packed separation column, a compressor, a heat exchanger, a cooling tower, a pressure swing adsorption (PSA) unit, etc.

The steam cracker product stream can also comprise water (from the steam used in the liquid steam cracker furnace section), wherein the water can be condensed and separated from the steam cracker product stream, for example in a quench tower. The water recovered from the steam cracker product stream can be further converted into steam and it can be recycled to the gas steam cracker furnace.

In an aspect, the process for producing olefins as disclosed herein can further comprise recovering at least a portion of ethylene from the olefin gas stream 50 to produce recovered ethylene. In some aspects, at least a portion of the recovered ethylene can be polymerized to produce a polymer product, such as polyethylene, an ethylene copolymer, an ethylene oligomer, etc.

In an aspect, the process for producing olefins as disclosed herein can further comprise recovering at least a portion of propylene from the olefin gas stream 50 to produce recovered propylene. In some aspects, at least a portion of the recovered propylene can be polymerized to produce a polymer product, such as polypropylene, a propylene copolymer, a propylene oligomer, etc.

In some aspects, two or more separation units independently selected from the group consisting of the first separation unit 300, the second separation unit 150, and the steam cracker separation unit can be the same separation unit. For example, the first separation unit 300 and the second separation unit 150 can be the same separation unit. As another example, the first separation unit 300 and the steam cracker separation unit can be the same separation unit. As yet another example, the second separation unit 150 and the steam cracker separation unit can be the same separation unit. As still yet another example, the first separation unit 300, the second separation unit 150, and the steam cracker separation unit can all be the same separation unit.

In an aspect, the process for producing olefins as disclosed herein can further comprise recycling at least a portion 41a of the first hydrogen stream 41, at least a portion 51a of the second hydrogen stream 51, at least a portion of the third hydrogen stream 16, or combinations thereof to the hydrogenolysis reactor 100 and/or the hydrocracking reactor 200. For example, at least a portion 41a of the first hydrogen stream 41 can be recycled via streams 55, 55b to the hydrogenolysis reactor 100 and/or via streams 55, 55a to the hydrocracking reactor 200. As another example, at least a portion 51a of the second hydrogen stream 51 can be recycled via streams 55, 55b to the hydrogenolysis reactor 100 and/or via streams 55, 55a to the hydrocracking reactor 200. As yet another example, at least a portion of the third hydrogen stream 16 can be recycled via stream 16b to the hydrogenolysis reactor 100 and/or via stream 16a to the hydrocracking reactor 200.

In an aspect, the process for producing olefins as disclosed herein can further comprise feeding at least a portion 18a of the second $C_{2+}$ gas stream 18 to the gas steam cracker 400, for example via stream 56. In an aspect, the process for producing olefins as disclosed herein can further comprise feeding at least a portion 53a of the saturated gas stream 53 to the gas steam cracker 400, for example via stream 56. The second $C_{2+}$ gas stream 18 and/or the saturated gas stream 53 can be separated into an ethane stream and a propane stream, wherein the ethane stream can be fed to the first cracking zone of the gas steam cracker furnace, and wherein the propane stream can be fed to the second cracking zone of the gas steam cracker furnace, as previously described herein. As will be appreciated by one of skill in the art, and with the help of this disclosure, in order to produce on-spec ethylene, ethane and propane resulting from a steam cracking process are generally separated into an ethane stream and a propane stream (e.g., ethane comes from a $C_2$ splitter and propane comes from a $C_3$ splitter). Further, and as will be appreciated by one of skill in the art, and with the help of this disclosure, the ethane stream and the propane stream could be mixed together prior to recycling to the steam cracker, at the expense of cracking one of the components at sub-optimal conditions; which could be desired in the case of steam crackers that are constrained by the furnace capacity (e.g., number of furnaces). However, when ethane and propane are feedstocks to the steam cracking furnaces (as opposed to recycle streams in a steam cracking process), ethane and propane could be cracked together, or separated prior to cracking.

In an aspect, the process for producing olefins as disclosed herein, and for example as illustrated in FIG. 1, can comprise (a) introducing a butane feed stream 10 and hydrogen 15 to a hydrogenolysis reactor 100 to produce a hydrogenolysis product stream 20, wherein the hydrogenolysis reactor 100 comprises a hydrogenolysis supported bimetallic catalyst, wherein the hydrogenolysis bimetallic supported catalyst comprises Pt and Ir supported on ZSM-5, wherein the hydrogenolysis reactor 100 is characterized by a temperature of less than about 330° C., wherein the hydrogenolysis reactor 100 is characterized by an i-butane conversion of less than about 25%, wherein the butane feed stream comprises n-butane and i-butane, wherein the butane feed stream is characterized by a mole ratio of n-butane to i-butane of equal to or greater than about 1:1, and wherein the hydrogenolysis product stream 20 comprises hydrogen, methane, ethane, propane, i-butane, and optionally n-butane;

(b) separating at least a portion 20a of the hydrogenolysis product stream 20 in a second separation unit 150 into a third hydrogen-containing stream 16, optionally a third methane stream 17, a second $C_{2+}$ gas stream 18, and a second $C_4s$ stream 19, wherein the second $C_{2+}$ gas stream 18 comprises ethane and propane, and wherein the second $C_4s$ stream 19 comprises i-butane, and optionally n-butane; (c) feeding at least a portion of the second $C_4s$ stream 19 and optionally at least a portion of the hydrogenolysis product stream 20, and hydrogen 25 to a hydrocracking reactor 200 to produce a hydrocracking product stream 30, wherein the hydrocracking reactor 200 comprises a hydrocracking catalyst, wherein the hydrocracking reactor 200 is characterized by a temperature of equal to or greater than about 350° C., wherein the hydrocracking product stream 30 comprises hydrogen, methane, ethane, propane, i-butane, and optionally n-butane, and wherein the amount of ethane in the hydrocracking product stream 30 is greater than the amount of ethane in the hydrogenolysis product stream 20; (d) separating at least a portion of the hydrocracking product stream 30 in a first separation unit 300 into a first hydrogen stream 41, a first methane stream 42, a first $C_{2+}$ gas stream 40, a first $C_4s$ stream 43, and optionally a $C_{5+}$ stream 44, wherein the first $C_{2+}$ gas stream 40 comprises ethane and propane, and wherein the first $C_4s$ stream 43 comprises i-butane, and optionally n-butane; (e) feeding at least a portion of the first $C_{2+}$ gas stream 40 and optionally at least a portion 18a of the second $C_{2+}$ gas stream 18 to a gas steam cracker 400 to produce a steam cracker product stream, wherein the steam cracker product stream comprises olefins, wherein the amount of olefins in the steam cracker product stream is greater than the amount of olefins in the first $C_{2+}$ gas stream 40, and optionally the second $C_{2+}$ gas stream 18, and wherein the olefins comprise ethylene and propylene in a weight ratio of ethylene to propylene of equal to or greater than about 5:1; (f) separating at least a portion of the steam cracker product stream in a steam cracker separation unit into an olefin gas stream 50, a second hydrogen stream 51, a second methane stream 52, and a saturated gas stream 53; wherein the olefin gas stream 50 comprises ethylene and propylene; and wherein the saturated gas stream 53 comprises ethane and propane; (g) optionally introducing at least a portion of the second $C_4s$ stream 19 and/or at least a portion of the first $C_4s$ stream 43 to the hydrogenolysis reactor 100 and/or the hydrocracking reactor 200; and (h) optionally recycling at least a portion of the first hydrogen stream 41, at least a portion of the second hydrogen stream 51, at least a portion of the third hydrogen stream 16, or combinations thereof to the hydrogenolysis reactor 100 and/or the hydrocracking reactor 200.

In an aspect, a process for producing olefins as disclosed herein can advantageously display improvements in one or more method characteristics when compared to an otherwise similar process that lacks a step of introducing a butane feed stream and hydrogen to a hydrogenolysis reactor (e.g., an otherwise similar process that uses a hydrocracking reactor only, and no hydrogenolysis reactor). Conventionally, field-grade butane streams are steam cracked directly; which creates relatively low quantities of ethylene and many by-products, which in turn require a costly separation section to recover ethylene. Also conventionally, field-grade butane streams can be sent to a hydrocracking reactor to create a stream containing ethane and propane, which is then fed to a steam cracker; however, the amount of ethane, and thus ethylene in this conventional process is much less than in the process for producing olefins as disclosed herein.

In an aspect, a process for producing olefins as disclosed herein can advantageously provide for more ethane that can be fed to a gas cracker to create ethylene; when compared to an otherwise similar process that lacks a step of introducing a butane feed stream and hydrogen to a hydrogenolysis reactor (e.g., an otherwise similar process that uses a hydrocracking reactor only, and no hydrogenolysis reactor). As will be appreciated by one of skill in the art, and with the help of this disclosure, ethane is the most favorable feed to maximize ethylene production in a steam cracker, and propylene is a by-product when ethylene is the desired product in steam cracking.

In an aspect, a process for producing olefins as disclosed herein can advantageously produce more ethylene than an otherwise similar process that lacks a step of introducing a butane feed stream and hydrogen to a hydrogenolysis reactor (e.g., an otherwise similar process that uses a hydrocracking reactor only, and no hydrogenolysis reactor). Additional advantages of the process for producing olefins as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

The distribution of products was investigated for an olefin production system similar to the olefins production system 1000 of FIG. 1, by contrast with conventional methods of producing olefins from field-grade butane streams. The data are displayed in FIG. 2. The data in FIG. 2 were estimated using a SPYRO® program which can estimate the cracking yields from a steam cracker from various feedstock inputs and various cracking temperature inputs. As will be appreciated by one of skill in the art, and with the help of this disclosure, SPYRO estimates are generally considered accurate.

Field-grade butane streams are typically a mixture of n-butane and i-butane, optionally with trace amounts of other hydrocarbons, such as butenes, $C_3s$, $C_5s$, etc. A typical ratio can be 70% n-butane/30% i-butane.

A conventional method for the production of olefins from a field-grade butane stream is to send the feed to a butane steam cracker, which method produces a variety of products and about 36 wt. % ethylene.

An alternative conventional method is to subject the entire field-grade butane stream to hydrocracking, thus producing a mixture of methane, ethane, and propane; wherein the ethane and propane can be further sent to a gas cracker to create olefins; which method produces about 58 wt. % ethylene.

Figure 2:
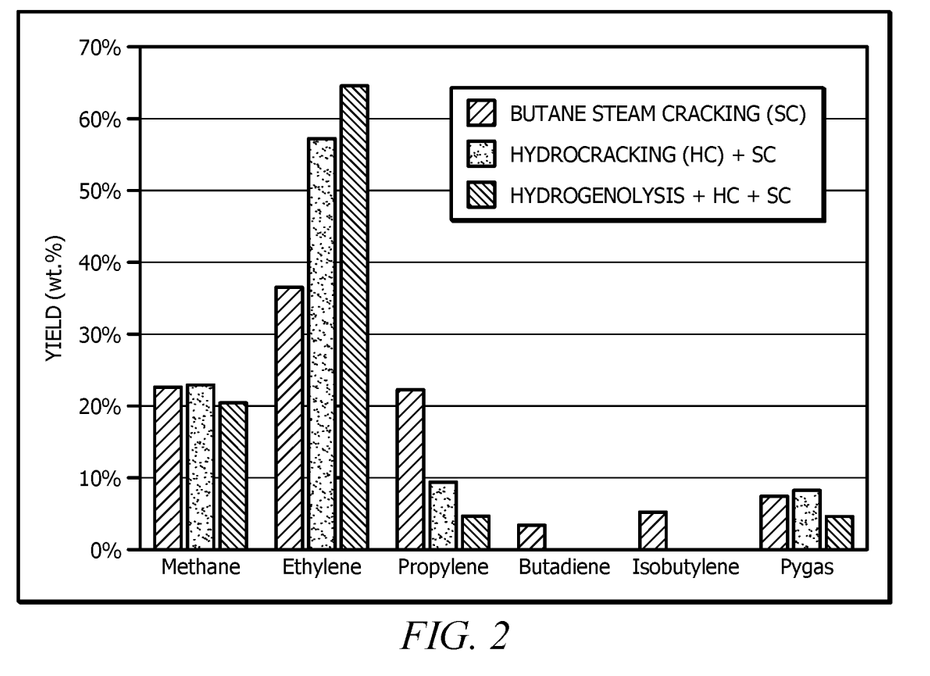
FIG. 2 displays a graph of various products yields in different olefins production systems.

In the case of hydrocracking followed by steam cracking, as well as in the case of hydrogenolysis integrated with hydrocracking and steam cracking, the amount of butadiene and isobutylene produced is so small (as shown in FIG. 2) that it is not worth separating it out and collecting. The $C_4s$ in these two cases are hydrogenated and blended in with the fresh field butane feed. In addition to the products displayed in FIG. 2, Hz, pyoil and $CO_2$ are also produced. The lower amount of methane produced by hydrogenolysis integrated with hydrocracking and steam cracking is indicative of the greater carbon efficiency of this combined process, whereby a higher amount of the $C_4$ feed is converted into valuable/collectable products.

Figure 3:
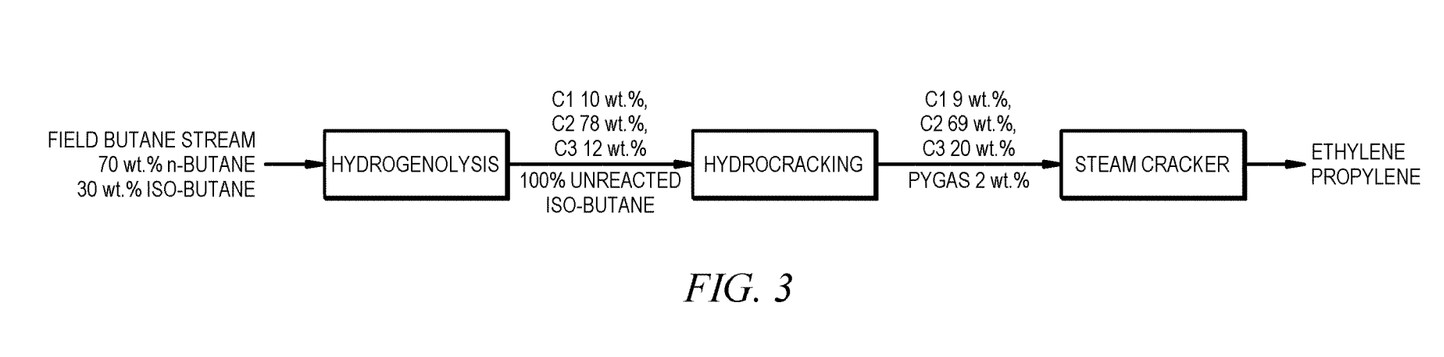
FIG. 3 displays another configuration of an olefins production system.

The process for producing olefins as disclosed herein, for example as illustrated in FIG. 3, wherein the field-grade butane stream is subjected to selective hydrogenolysis, followed by hydrocracking, and then by steam cracking, can produce about 70 wt. % ethylene.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

ADDITIONAL DISCLOSURE

A first aspect which is a process comprising: (a) introducing a butane feed stream and hydrogen to a hydrogenolysis reactor to produce a hydrogenolysis product stream, wherein the hydrogenolysis reactor comprises a hydrogenolysis catalyst, wherein the butane feed stream comprises n-butane and i-butane, and wherein the hydrogenolysis product stream comprises hydrogen, methane, ethane, propane, i-butane, and optionally n-butane; and (b) feeding at least a portion of the hydrogenolysis product stream and hydrogen to a hydrocracking reactor to produce a hydrocracking product stream, wherein the hydrocracking reactor comprises a hydrocracking catalyst, wherein the hydrocracking product stream comprises hydrogen, methane, ethane, propane, i-butane, optionally n-butane, optionally $C_5$ hydrocarbons, and optionally $C_{6+}$ aromatic hydrocarbons, wherein the amount of i-butane in the hydrocracking product stream is less than the amount of i-butane in the hydrogenolysis product stream, and wherein the amount of ethane in the hydrocracking product stream is greater than the amount of ethane in the hydrogenolysis product stream.

A second aspect, which is the process of the first aspect, wherein the n-butane is present in the butane feed stream in an amount of equal to or greater than about 50 mol %.

A third aspect, which is the process of the first and the second aspects, further comprising (i) separating at least a portion of the hydrocracking product stream in a first separation unit into a first hydrogen stream, a first methane stream, a first $C_{2+}$ gas stream, a first $C_4$s stream, and optionally a $C_{5+}$ stream, wherein the first $C_{2+}$ gas stream comprises ethane and propane, wherein the first $C_4$s stream comprises i-butane, and optionally n-butane, and wherein the $C_{5+}$ stream comprises $C_5$ hydrocarbons, and optionally $C_{6+}$ aromatic hydrocarbons; (ii) feeding at least a portion of the first $C_{2+}$ gas stream to a gas steam cracker furnace to produce a steam cracker product stream, wherein the steam cracker product stream comprises olefins, wherein the amount of olefins in the steam cracker product stream is greater than the amount of olefins in the first $C_{2+}$ gas stream, and wherein the olefins comprise ethylene and propylene; and (iii) optionally feeding at least a portion of the first $C_4$s stream to the hydrocracking reactor.

A fourth aspect, which is the process of any of the first through the third aspects, further comprising (i) separating at least a portion of the hydrogenolysis product stream in a second separation unit into a third hydrogen-containing stream, optionally a third methane stream, a second $C_{2+}$ gas stream, and a second $C_4$s stream, wherein the second $C_{2+}$ gas stream comprises ethane and propane, and wherein the second $C_4$s stream comprises i-butane, and optionally n-butane; (ii) feeding at least a portion of the second $C_4$s stream to the hydrocracking reactor; and (iii) optionally feeding at least a portion of the second $C_{2+}$ gas stream to the gas steam cracker furnace.

A fifth aspect, which is the process of the fourth aspect, wherein the first $C_4$s stream and/or the second $C_4$s stream comprise n-butane; and wherein at least a portion of the first $C_4$s stream and/or at least a portion of the second $C_4$s stream are separated into an i-butane stream and an n-butane stream.

A sixth aspect, which is the process of the fifth aspect, further comprising (i) feeding at least a portion of the i-butane stream to the hydrocracking reactor; and/or (ii) feeding at least a portion of the n-butane stream to the hydrogenolysis reactor.

A seventh aspect, which is the process of any of the first through the sixth aspects, wherein the hydrogenolysis reactor is characterized by a temperature of from about 200° C. to about 330° C.; a pressure of from about 0 psig to about 300 psig; a hydrocarbon-based weight hourly space velocity (WHSV) of from about 0.1 $h^{-1}$ to about 15 $h^{-1}$; and a hydrogen to $C_4$ hydrocarbons molar ratio of from about 1:1 to about 10:1.

An eighth aspect, which is the process of any of the first through the seventh aspects, wherein the hydrogenolysis catalyst comprises a hydrogenolysis monometallic supported catalyst and/or a hydrogenolysis bimetallic supported catalyst; wherein the hydrogenolysis monometallic supported catalyst comprises a zeolite-supported monometallic catalyst and/or an alumina-supported monometallic catalyst; wherein the hydrogenolysis bimetallic supported catalyst comprises a zeolite-supported bimetallic catalyst and/or an alumina-supported bimetallic catalyst; wherein the hydrogenolysis bimetallic supported catalyst comprises a first metal and a second metal, wherein the first metal and the second metal are different; wherein the hydrogenolysis monometallic supported catalyst comprises a third metal; wherein the third metal is the same as or different from the first metal and/or the second metal; wherein the first metal, the second metal, and the third metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co); wherein the support comprises alumina and/or a zeolite; wherein the zeolite is selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof; and wherein the support optionally comprises a binder comprising alumina, titania, silica, or combinations thereof.

A ninth aspect, which is the process of any of the first through the eighth aspects, wherein the hydrogenolysis catalyst comprises Pt and Ir supported on ZSM-5.

A tenth aspect, which is the process of any of the first through the ninth aspects, wherein the hydrocracking reactor is characterized by a temperature of from about 350° C. to about 600° C.; a pressure of from about 10 psig to about 300 psig; a hydrocarbon-based weight hourly space velocity (WHSV) of from about 0.1 h$^{-1}$ to about 10 h$^{-1}$; a hydrogen to $C_4$ hydrocarbons molar ratio of from about 0.75:1 to about 10:1; and wherein the hydrocracking catalyst comprises one or more metals on a support, wherein the one or more metals comprise Pd, Pt, Ni, Co, Mn, Fe, Rh, Ir, Ru, W, Zr, or combinations thereof; wherein the support comprises a zeolite, ZSM-5, zeolite Y, mordenite, zeolite L, ZSM-22, ZSM-11, chabazite, ferrierite, zeolite beta, silated ZSM-5, zirconia, sulfated zirconia, alumina, or combinations thereof; and wherein the hydrogenolysis catalyst and the hydrocracking catalyst are the same or different.

An eleventh aspect, which is the process of any of the first through the tenth aspects, comprising (i) separating at least a portion of the steam cracker product stream in a steam cracker separation unit into a second hydrogen stream, a second methane stream, an olefin gas stream, and a saturated gas stream; wherein the olefin gas stream comprises ethylene and propylene; and wherein the saturated gas stream comprises ethane and propane; (ii) optionally recycling at least a portion of the first hydrogen stream, at least a portion of the second hydrogen stream, at least a portion of the third hydrogen stream, or combinations thereof to the hydrogenolysis reactor and/or the hydrocracking reactor; and (iii) optionally recycling at least a portion of the saturated gas stream to the gas steam cracker furnace.

A twelfth aspect, which is the process of any of the first through the eleventh aspects, wherein the gas steam cracker furnace comprises a first cracking zone and a second cracking zone, wherein the first cracking zone is characterized by an ethane cracking temperature, wherein the second cracking zone is characterized by a propane cracking temperature, and wherein the ethane cracking temperature is greater than the propane cracking temperature.

A thirteenth aspect, which is the process of the twelfth aspect, further comprising (i) separating at least a portion of the first $C_{2+}$ gas stream, at least a portion of the second $C_{2+}$ gas stream, at least a portion of the saturated gas stream, or combinations thereof into an ethane stream and a propane stream; (ii) feeding at least a portion of the ethane stream to the first cracking zone, and (iii) feeding at least a portion of the propane stream to the second cracking zone.

A fourteenth aspect, which is the process of any of the first through the thirteenth aspects, wherein two or more separation units independently selected from the group consisting of the first separation unit, the second separation unit, and the steam cracker separation unit are the same separation unit.

A fifteenth aspect, which is the process of any of the first through the fourteenth aspects, wherein the hydrogenolysis reactor is characterized by an i-butane conversion of less than about 25%.

A sixteenth aspect, which is the process of any of the first through the fifteenth aspects, wherein the hydrogenolysis reactor is characterized by a n-butane conversion of equal to or greater than about 90%.

A seventeenth aspect, which is the process of any of the first through the sixteenth aspects, wherein an ethylene to propylene weight ratio in the steam cracker product stream is increased by equal to or greater than about 10% when compared to an ethylene to propylene weight ratio in a steam cracker product stream in an otherwise similar process that lacks the step (a) of introducing a butane feed stream and hydrogen to a hydrogenolysis reactor.

An eighteenth aspect, which is the process of any of the first through the seventeenth aspects, wherein an ethylene to propylene weight ratio in the steam cracker product stream is equal to or greater than about 4:1.

A nineteenth aspect, which is the process of any of the first through the eighteenth aspects, wherein an ethane to propane weight ratio in the hydrocracking product stream is increased by equal to or greater than about 10% when compared to an ethane to propane weight ratio in a hydrocracking product stream in an otherwise similar process that lacks the step (a) of introducing a butane feed stream and hydrogen to a hydrogenolysis reactor.

A twentieth aspect, which is a process for producing olefins comprising: (a) introducing a butane feed stream and hydrogen to a hydrogenolysis reactor to produce a hydrogenolysis product stream, wherein the hydrogenolysis reactor comprises a hydrogenolysis supported bimetallic catalyst, wherein the hydrogenolysis bimetallic supported catalyst comprises Pt and Ir supported on ZSM-5, wherein the hydrogenolysis reactor is characterized by a temperature of less than about 330° C., wherein the hydrogenolysis reactor is characterized by an i-butane conversion of less than about 25%, wherein the butane feed stream comprises n-butane and i-butane, wherein the butane feed stream is characterized by a mole ratio of n-butane to i-butane of equal to or greater than about 1:1, and wherein the hydrogenolysis product stream comprises hydrogen, methane, ethane, propane, and i-butane; (b) feeding at least a portion of the hydrogenolysis product stream and hydrogen to a hydrocracking reactor to produce a hydrocracking product stream, wherein the hydrocracking reactor comprises a hydrocracking catalyst, wherein the hydrocracking reactor is characterized by a temperature of equal to or greater than about 350° C., wherein the hydrocracking product stream comprises hydrogen, methane, ethane, propane, i-butane, optionally $C_5$ hydrocarbons, and optionally $C_{6+}$ aromatic hydrocarbons, and wherein the amount of ethane in the hydrocracking product stream is greater than the amount of ethane in the hydrogenolysis product stream; (c) separating at least a portion of the hydrocracking product stream in a separation unit into a first hydrogen stream, a first methane stream, a first $C_{2+}$ gas stream, a butane stream, and optionally a $C_{5+}$ stream, wherein the first $C_{2+}$ gas stream comprises ethane and propane, wherein the butane stream comprises i-butane, and wherein the $C_{5+}$ stream comprises $C_5$ hydrocarbons, and optionally $C_{6+}$ aromatic hydrocarbons; (d) feeding at least a portion of the first $C_{2+}$ gas stream to a gas steam cracker furnace to produce a steam cracker product stream, wherein the steam cracker product stream comprises olefins, wherein the amount of olefins in the steam cracker product stream is greater than the amount of olefins in the first $C_{2+}$ gas stream, and wherein the olefins comprise ethylene and propylene in a weight ratio of ethylene to propylene of equal to or greater than about 5:1; and (e) recycling at least a portion of the butane stream to the hydrocracking reactor; recycling at least a portion of the first hydrogen stream to the hydrogenolysis reactor and/or the hydrocracking reactor; or both.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process comprising:
   (a) introducing a butane feed stream and hydrogen to a hydrogenolysis reactor to produce a hydrogenolysis product stream, wherein the hydrogenolysis reactor comprises a hydrogenolysis catalyst, wherein the hydrogenolysis reactor is characterized by a temperature of from about 200° C. to about 330° C., wherein the butane feed stream comprises n-butane and i-butane, wherein the n-butane is present in the butane feed stream in an amount of equal to or greater than about 50 mol %, wherein the hydrogenolysis reactor is characterized by an i-butane conversion of less than about 25%, wherein the hydrogenolysis reactor is characterized by a n-butane conversion of equal to or greater than about 90%, and wherein the hydrogenolysis product stream comprises hydrogen, methane, ethane, propane, i-butane, and optionally n-butane; and
   (b) feeding at least a portion of the hydrogenolysis product stream and hydrogen to a hydrocracking reactor to produce a hydrocracking product stream, wherein the hydrocracking reactor comprises a hydrocracking catalyst, wherein the hydrocracking product stream comprises hydrogen, methane, ethane, propane, i-butane, optionally n-butane, optionally $C_5$ hydrocarbons, and optionally $C_{6+}$ aromatic hydrocarbons, wherein the amount of i-butane in the hydrocracking product stream is less than the amount of i-butane in the hydrogenolysis product stream, and wherein the amount of ethane in the hydrocracking product stream is greater than the amount of ethane in the hydrogenolysis product stream.

2. The process of claim 1 further comprising (i) separating at least a portion of the hydrocracking product stream in a first separation unit into a first hydrogen stream, a first methane stream, a first $C_{2+}$ gas stream, a first $C_4$s stream, and optionally a $C_{5+}$ stream, wherein the first $C_{2+}$ gas stream comprises ethane and propane, wherein the first $C_4$s stream comprises i-butane, and optionally n-butane, and wherein the $C_{5+}$ stream comprises $C_5$ hydrocarbons, and optionally $C_{6+}$ aromatic hydrocarbons; (ii) feeding at least a portion of the first $C_{2+}$ gas stream to a gas steam cracker furnace to produce a steam cracker product stream, wherein the steam cracker product stream comprises olefins, wherein the amount of olefins in the steam cracker product stream is greater than the amount of olefins in the first $C_{2+}$ gas stream, and wherein the olefins comprise ethylene and propylene; and (iii) optionally feeding at least a portion of the first $C_4$s stream to the hydrocracking reactor.

3. The process of claim 2, wherein the gas steam cracker furnace comprises a first cracking zone and a second cracking zone, wherein the first cracking zone is characterized by an ethane cracking temperature, wherein the second cracking zone is characterized by a propane cracking temperature, and wherein the ethane cracking temperature is greater than the propane cracking temperature.

4. The process of claim 3 further comprising (i) separating at least a portion of the first $C_{2+}$ gas stream, at least a portion of the second $C_{2+}$ gas stream, at least a portion of the saturated gas stream, or combinations thereof into an ethane stream and a propane stream; (ii) feeding at least a portion of the ethane stream to the first cracking zone, and (iii) feeding at least a portion of the propane stream to the second cracking zone.

5. The process of claim 2, wherein an ethylene to propylene weight ratio in the steam cracker product stream is increased by equal to or greater than about 10% when compared to an ethylene to propylene weight ratio in a steam cracker product stream in an otherwise similar process that lacks the step (a) of introducing a butane feed stream and hydrogen to a hydrogenolysis reactor.

6. The process of claim 2, wherein an ethylene to propylene weight ratio in the steam cracker product stream is equal to or greater than about 4:1.

7. The process of claim 2 further comprising (i) separating at least a portion of the hydrogenolysis product stream in a second separation unit into a third hydrogen-containing stream, optionally a third methane stream, a second $C_{2+}$ gas stream, and a second $C_4$s stream, wherein the second $C_{2+}$ gas stream comprises ethane and propane, and wherein the second $C_4$s stream comprises i-butane, and optionally n-butane; (ii) feeding at least a portion of the second $C_4$s stream to the hydrocracking reactor; and (iii) optionally feeding at least a portion of the second $C_{2+}$ gas stream to the gas steam cracker furnace.

8. The process of claim 7, wherein the first $C_4$s stream and/or the second $C_4$s stream comprise n-butane; and wherein at least a portion of the first $C_4$s stream and/or at least a portion of the second $C_4$s stream are separated into an i-butane stream and an n-butane stream.

9. The process of claim 8 further comprising (i) feeding at least a portion of the i-butane stream to the hydrocracking reactor; and/or (ii) feeding at least a portion of the n-butane stream to the hydrogenolysis reactor.

10. The process of claim 7 comprising (i) separating at least a portion of the steam cracker product stream in a steam cracker separation unit into a second hydrogen stream, a second methane stream, an olefin gas stream, and a saturated gas stream; wherein the olefin gas stream comprises ethylene and propylene; and wherein the saturated gas stream comprises ethane and propane; (ii) optionally recycling at least a portion of the first hydrogen stream, at least a portion of the second hydrogen stream, at least a portion of the third hydrogen stream, or combinations thereof to the hydrogenolysis reactor and/or the hydrocracking reactor; and (iii)

optionally recycling at least a portion of the saturated gas stream to the gas steam cracker furnace.

11. The process of claim 1, wherein the hydrogenolysis reactor is characterized by a pressure of from about 0 psig to about 300 psig; a hydrocarbon-based weight hourly space velocity (WHSV) of from about 0.1 $h^{-1}$ to about 15 $h^{-1}$; and a hydrogen to $C_4$ hydrocarbons molar ratio of from about 1:1 to about 10:1.

12. The process of claim 1, wherein the hydrogenolysis catalyst comprises a hydrogenolysis monometallic supported catalyst and/or a hydrogenolysis bimetallic supported catalyst; wherein the hydrogenolysis monometallic supported catalyst comprises a zeolite-supported monometallic catalyst and/or an alumina-supported monometallic catalyst; wherein the hydrogenolysis bimetallic supported catalyst comprises a zeolite-supported bimetallic catalyst and/or an alumina-supported bimetallic catalyst; wherein the hydrogenolysis bimetallic supported catalyst comprises a first metal and a second metal, wherein the first metal and the second metal are different; wherein the hydrogenolysis monometallic supported catalyst comprises a third metal; wherein the third metal is the same as or different from the first metal and/or the second metal; wherein the first metal, the second metal, and the third metal can each independently be selected from the group consisting of iridium (Ir), platinum (Pt), rhodium (Rh), ruthenium (Ru), palladium (Pd), molybdenum (Mo), tungsten (W), nickel (Ni), and cobalt (Co); wherein the support comprises alumina and/or a zeolite; wherein the zeolite is selected from the group consisting of ZSM-5, ZSM-11, Y, high-silica Y, USY, EU-1, EU-2, beta, L, ferrierite, CHA, SSZ-16, Nu-3, Sigma-1, Silicalite-1, and combinations thereof and wherein the support optionally comprises a binder comprising alumina, titania, silica, or combinations thereof.

13. The process of claim 1, wherein the hydrogenolysis catalyst comprises Pt and Ir supported on ZSM-5.

14. The process of claim 1, wherein the hydrocracking reactor is characterized by a temperature of from about 350° C. to about 600° C.; a pressure of from about 10 psig to about 300 psig; a hydrocarbon-based weight hourly space velocity (WHSV) of from about 0.1 $h^{-1}$ to about 10 $h^{-1}$; a hydrogen to $C_4$ hydrocarbons molar ratio of from about 0.75:1 to about 10:1; and wherein the hydrocracking catalyst comprises one or more metals on a support, wherein the one or more metals comprise Pd, Pt, Ni, Co, Mn, Fe, Rh, Ir, Ru, W, Zr, or combinations thereof wherein the support comprises a zeolite, ZSM-5, zeolite Y, mordenite, zeolite L, ZSM-22, ZSM-11, chabazite, ferrierite, zeolite beta, silated ZSM-5, zirconia, sulfated zirconia, alumina, or combinations thereof; and wherein the hydrogenolysis catalyst and the hydrocracking catalyst are the same or different.

15. The process of claim 10, wherein two or more separation units independently selected from the group consisting of the first separation unit, the second separation unit, and the steam cracker separation unit are the same separation unit.

16. The process of claim 1, wherein an ethane to propane weight ratio in the hydrocracking product stream is increased by equal to or greater than about 10% when compared to an ethane to propane weight ratio in a hydrocracking product stream in an otherwise similar process that lacks the step (a) of introducing a butane feed stream and hydrogen to a hydrogenolysis reactor.

17. A process for producing olefins comprising:
(a) introducing a butane feed stream and hydrogen to a hydrogenolysis reactor to produce a hydrogenolysis product stream, wherein the hydrogenolysis reactor comprises a hydrogenolysis supported bimetallic catalyst, wherein the hydrogenolysis bimetallic supported catalyst comprises Pt and Ir supported on ZSM-5, wherein the hydrogenolysis reactor is characterized by a temperature of less than about 330° C., wherein the hydrogenolysis reactor is characterized by an i-butane conversion of less than about 25%, wherein the hydrogenolysis reactor is characterized by a n-butane conversion of equal to or greater than about 90%, wherein the butane feed stream comprises n-butane and i-butane, wherein the butane feed stream is characterized by a mole ratio of n-butane to i-butane of equal to or greater than about 1:1, and wherein the hydrogenolysis product stream comprises hydrogen, methane, ethane, propane, and i-butane;
(b) feeding at least a portion of the hydrogenolysis product stream and hydrogen to a hydrocracking reactor to produce a hydrocracking product stream, wherein the hydrocracking reactor comprises a hydrocracking catalyst, wherein the hydrocracking reactor is characterized by a temperature of equal to or greater than about 350° C., wherein the hydrocracking product stream comprises hydrogen, methane, ethane, propane, i-butane, optionally $C_5$ hydrocarbons, and optionally $C_{6+}$ aromatic hydrocarbons, and wherein the amount of ethane in the hydrocracking product stream is greater than the amount of ethane in the hydrogenolysis product stream;
(c) separating at least a portion of the hydrocracking product stream in a separation unit into a first hydrogen stream, a first methane stream, a first $C_{2+}$ gas stream, a butane stream, and optionally a $C_{5+}$ stream, wherein the first $C_{2+}$ gas stream comprises ethane and propane, wherein the butane stream comprises i-butane, and wherein the $C_{5+}$ stream comprises $C_5$ hydrocarbons, and optionally $C_{6+}$ aromatic hydrocarbons;
(d) feeding at least a portion of the first $C_{2+}$ gas stream to a gas steam cracker furnace to produce a steam cracker product stream, wherein the steam cracker product stream comprises olefins, wherein the amount of olefins in the steam cracker product stream is greater than the amount of olefins in the first $C_{2+}$ gas stream, and wherein the olefins comprise ethylene and propylene in a weight ratio of ethylene to propylene of equal to or greater than about 5:1; and
(e) recycling at least a portion of the butane stream to the hydrocracking reactor; recycling at least a portion of the first hydrogen stream to the hydrogenolysis reactor and/or the hydrocracking reactor; or both.

18. The process of claim 17, wherein an ethane to propane weight ratio in the hydrocracking product stream is increased by equal to or greater than about 15% when compared to an ethane to propane weight ratio in a hydrocracking product stream in an otherwise similar process that lacks the step (a) of introducing a butane feed stream and hydrogen to a hydrogenolysis reactor.

19. The process of claim 17, wherein the hydrogenolysis reactor is characterized by a temperature of from about 280° C. to about 310° C.

20. The process of claim 17, wherein the hydrogenolysis reactor is characterized by an i-butane conversion of less than about 10%, and wherein the hydrogenolysis reactor is characterized by a n-butane conversion of equal to or greater than about 95%.

* * * * *